United States Patent [19]
Skogley

[11] Patent Number: 5,355,736
[45] Date of Patent: Oct. 18, 1994

[54] ABSORBER DEVICE AND PROCESS FOR USING SAME

[76] Inventor: Earl O. Skogley, 3535 Stucky Rd., Bozeman, Mont. 59715

[21] Appl. No.: 821,474

[22] Filed: Jan. 14, 1992

[51] Int. Cl.$^5$ .................... E21B 49/00; G01N 1/10; G01N 30/00
[52] U.S. Cl. .................... 73/863.21; 73/64.56; 73/863.23; 436/178
[58] Field of Search .......... 73/64.56, 863.21, 863.23; 436/178

[56] References Cited

U.S. PATENT DOCUMENTS

| | | | |
|---|---|---|---|
| 3,846,077 | 11/1974 | Ohringer | 73/863.23 |
| 3,987,677 | 10/1976 | Alter | 73/863.21 |
| 4,399,629 | 8/1983 | Duncan | 73/863.23 |
| 4,646,577 | 3/1987 | Phillips | 73/863.23 |
| 4,790,857 | 12/1988 | Miksch | 73/863.21 |
| 4,961,916 | 10/1990 | Lesage et al. | 73/863.21 |
| 4,993,874 | 2/1991 | Klusman | 73/863.21 |

OTHER PUBLICATIONS

Selton et al., "Rubber Disk Passive Monitor for Benzene Dosimeter," Analytical Chemistry, vol. 53, No. 3, Mar. 1981, pp. 458–461.
Dan Binkley and Pamela Matson, "Ion Exchange Resin Bag Method For Assessing Forest Soil Nitrogen Availability", Soil Sci. Soc. Am. J., vol. 47, 1050–1052 (1983).
Jae E. Yang, Earl O. Skogley, and Bernard E. Schaff, "Microwave Radiation and Incubation Effects on Resin–Extractable Nutrients: I. Nitrate, Ammonium, and Sulfur", Soil Science Society of America Journal, vol. 54, No. 6, 1639–1640 (Nov.–Dec. 1990).
E. O. Skogley, S. J. Georgitis, J. E. Yang, and B. E. Schaff, "The Phytoavailability Soil Test-PST", Commun. in Soil Sc. Plant Anal., 21(13–16), 1229–1243 (1990).
Stuart James Georgitis, "The Development and Characterization of the Phytoavailability Soil Test For Potassium, Sulfur, and Phosphorus", A thesis submitted in partial fulfillment of the requirements for the degree of Doctor of Philosophy in Crop and Soil Science, Montana State University, Bozeman, Montana, p. 13 (Jun. 1989).
E. O. Skogley, and B. E. Schaff, "Ion Diffusion in Soils As Related to Physical and Chemical Properties" Soil Science Society of America Journal, vol. 49, No. 4, 847–850 (Jul.–Aug. 1985).
B. E. Schaff, and E. O. Skogley, "Diffusion of Potassium, Calcium, and Magnesium in Bozeman Silt Loam as Influenced by Temperature and Moisture", Soil Science Society of America Journal, vol. 46, No. 3, 521–524 (May–Jun. 1982).
T. W. Massee, R. A. Olsen, and E. O. Skogley, "Characterizing Soil Fertility By Ion Diffusive Flux Measurements", Plant and Soil 47, 663–679 (1977).
No author listed, "Short Communication–A simple ion-exchange resin procedure for extracting plant-available elements from soil", Plant and Soil 46, 665–669 (1977).

*Primary Examiner*—Hezron E. Williams
*Assistant Examiner*—George M. Dombroske
*Attorney, Agent, or Firm*—Richard C. Conover

[57] ABSTRACT

An adsorber device for collecting diffusible ions in a liquid medium. The adsorber device includes an ion exchange "sink" comprising a hollow, spherical capsule filled with an ion exchange material or other adsorber. Further, the present invention includes a process for analyzing a test medium which includes scattering multiple adsorber devices throughout the test medium; recovering the devices after a predetermined amount of time; and leaching the accumulated solutes from the adsorber material to provide an extract solution which can then be analyzed by various procedures to determine quantities of accumulated solutes.

9 Claims, 13 Drawing Sheets

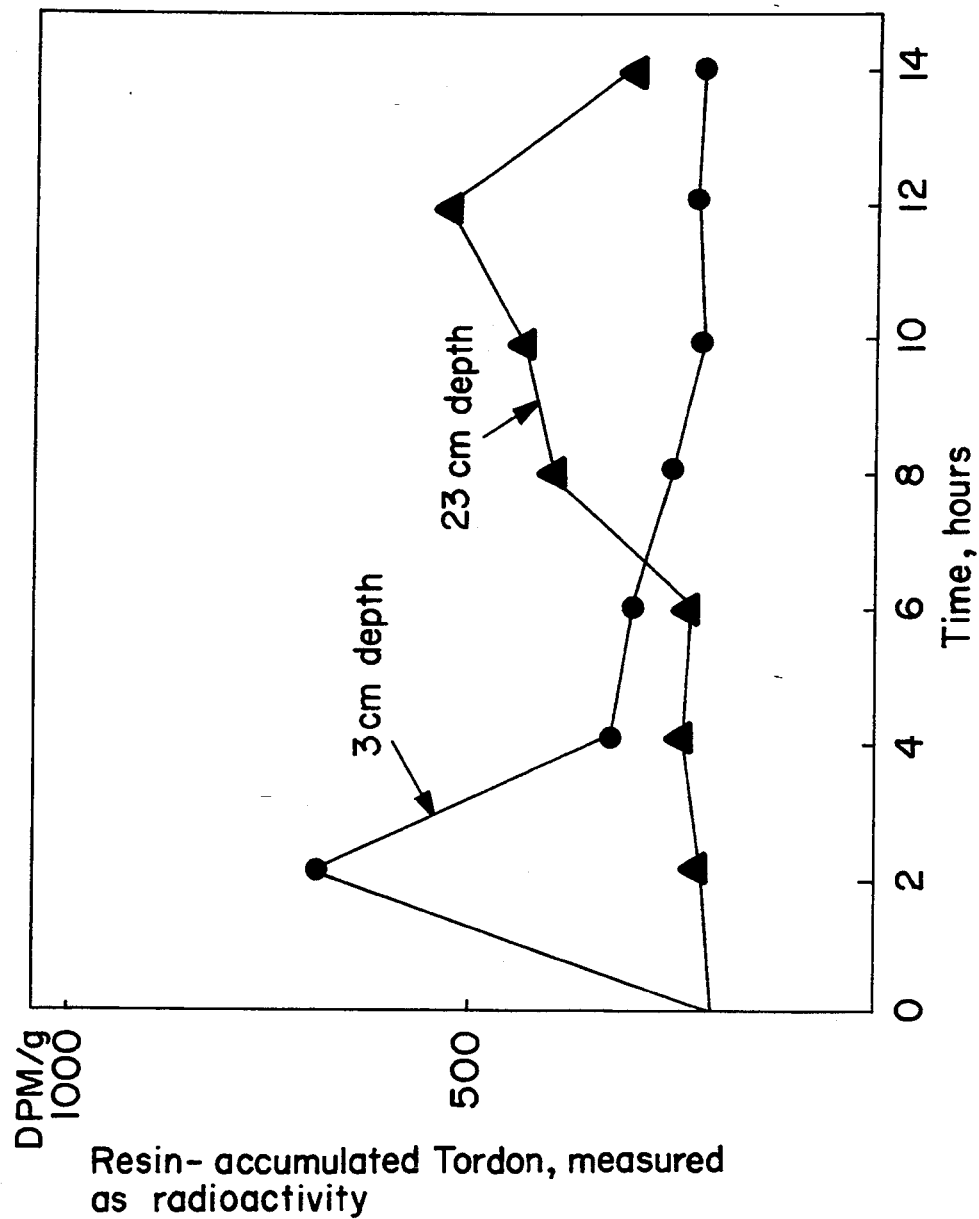

ABSORBER DEVICE AND PROCESS FOR USING SAME

BACKGROUND OF THE INVENTION

This invention relates to an improved adsorber device used in absorbing or measuring solutes in soils, water, solutions or other media having solution filled interstitial space. The improved adsorber utilizes porous shells housing an adsorber material with known chemical and physical characteristics.

Previous systems have been available to collect soil or water samples, but these systems are not easily adapted for testing the adsorption rate characteristics of solutes existing in the test media. Groundwater sampling systems, such as disclosed in U.S. Pat. No. 4,745,801 and U.S. Pat. No. 4,759,227, only collect groundwater samples and do not have an adsorbing material in the sampling apparatus to gather data on the adsorption rates or chemical make-up of the surrounding media. With systems such as those disclosed in the above listed patents, the sampling apparatus is connected to a remote data collection device located above the ground. The above mentioned sampling devices cannot be placed throughout a test site in a free-standing mode.

Other tools have been used to obtain soil samples directly by obtaining a small portion of the soil itself within a tool. Representative examples of soil sampling tools can be seen in U.S. Pat. No. 4,383,583 and U.S. Pat. No. 4,442,271. Although a soil sample provides a way for obtaining data through later soil analysis, such samples do not provide a convenient way for testing in-situ the defusibility, bioavailability, or uptake of specific solutes from soils, water, solutions, or other media. Removed soil samples provide information about conditions that may have existed up to the time the sample is taken, but this sampling technique is not readily adapted for analyzing on-going conditions that might exist after a soil sample is taken. In order to obtain a timed test using soil samples, a user would require an analysis on a sample taken at the beginning of the test and again on a sample taken at the end of a test to establish the net change taking place during the elapsed time of the test.

From the above it can be seen that a need exists for relatively small, free-standing adsorber devices which can be randomly placed within soil, water, or other medium, without the requirement for being connected to some other device positioned on the surface. The adsorber device should also have known adsorption characteristics and should be capable of detecting concentrations of selected ions, salts, or contaminants in solutions, standing water, or other media over time.

A further need exists for a sampler having uniform data collection characteristics. A plurality of data collection samplers, each having a uniform geometry, would permit conclusions to be drawn about the underlying conditions that might exist throughout the medium within a test site. A uniform geometry would greatly assist in the computer analysis of data obtained from any particular set of recovered samplers. This geometry would enable a user to compare results between different test sites and to calibrate the results from the sampler with those from "standard" procedures.

A need exists for apparatus and a process to collect diffusible ions simultaneously from adsorbers randomly scattered in the soil or places into samples previously collected. The present methods require several single element extractions as separate chemical procedures in order to obtain enough meaningful data for interpretation. The present invention would reduce time and material costs by replacing separate extractions with a single multi-element accumulation.

One example of a possible use of such an adsorber device would be to detect and absorb hydrocarbons leaking into soils surrounding buried storage containers.

Further such adsorber devices could be used to collect information as to the quantity of nutrients available for a plant to absorb from the surrounding soil as the plant grows.

An objective of the present invention is to provide apparatus and a process for analyzing quantities of diffusible ions available in the soil or the rate at which diffusible ions diffuse in the soil. Measurement of the extraction of elements from selected samples would give a quantitative definition of the diffusion rate of that particular element in that particular soil. Resulting data could be used, for example, to improve prediction accuracy of crop responses to fertilizer additions.

A further object is to provide apparatus and a process to measure the intensity factor of environmental availability of toxins. The intensity factor, is a function of toxin concentration and the ability of toxins to move through the medium. By measuring the intensity factor, information may be obtained to allow development of ranking criteria for potential threats of a toxin entering the food chain or contaminating ground water.

A further object is to provide apparatus and a process which may be used to evaluate and rank hazardous waste and other similar material such as mine tailings on the basis of the release rate of undesirable components.

A further object is to provide an apparatus and a process to be used as a first step in the purification of fluid extracts. It is desirable to have an adsorber device which may be placed into a solution to accumulate the free ions in the solution. The results of this process can be used to determine quantities of free ions in the solution.

A further object is to provide apparatus and a process to accumulate polar ions and certain non-polar molecules from liquid media such as petroleum products, paints, dyes, waters, waste waters, suspensions, natural and artificial soils, mine products, food products, nuclear power cooling waters, medicines, biological fluids, and others, as a means of determining quantities of ions and molecules in the medium.

A further object of the present invention is to provide apparatus and a process to accumulate diffusible solutes from waste-amended soil, to accumulate deleterious ions or chemicals from wells or other free-water sources such as lakes, streams, or from saturated soils or other porous media, in order to evaluate purity or quality aspects of the various media.

SUMMARY OF INVENTION

The present invention relates to an adsorber device for collecting diffusible ions from any liquid medium or solid medium having solution filled interstitial space. A principal component of the apparatus is an ion exchange "sink" comprising a hollow, spherical capsule filled with an ion exchange material or other adsorber.

The present invention includes a process for measuring the solutes in test media using such adsorber devices.

The present invention also includes a process for analyzing a test medium which includes scattering the multiple adsorber devices throughout the test medium; recovering the devices after a predetermined amount of time; and leaching the accumulated solutes from the adsorber material to provide an extract solution which can then be analyzed by various procedures to determine quantities of accumulated solutes.

BRIEF DESCRIPTION OF THE DRAWINGS

In order that the invention may be clearly understood and readily carried into effect, a preferred embodiment of the invention will now be described, by way of example only, with reference to the accompanying drawings wherein:

FIG. 8 is a graph showing detection of radioactive Tordon movement through a soil column according to Example 6.

DESCRIPTION OF A PREFERRED EMBODIMENT

Figure 1:
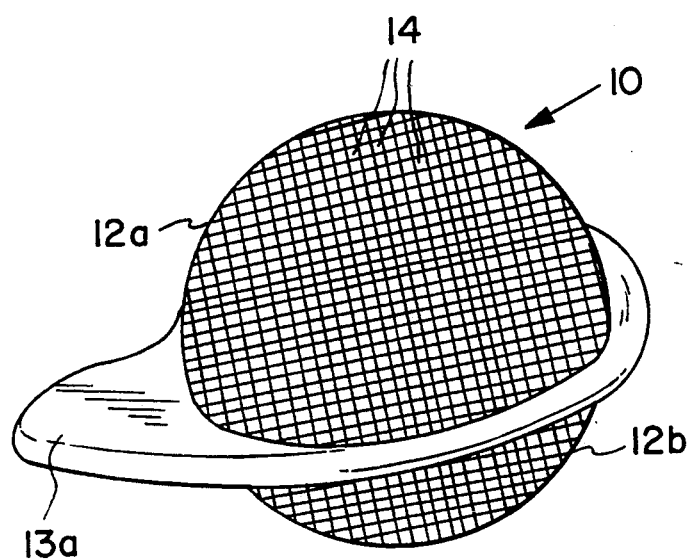
FIG. 1 is an enlarged perspective view of an adsorber according to the present invention.
Figure 2:
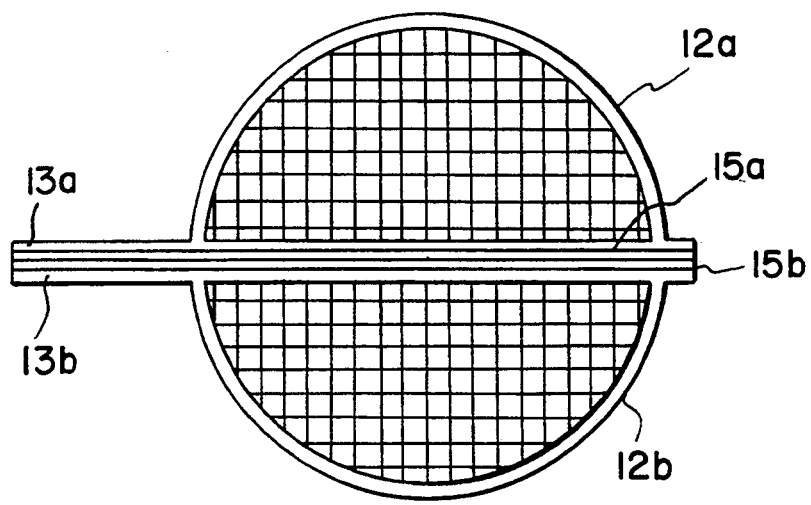
FIG. 2 is an elevational view of the adsorber shown in FIG. 1.
Figure 3:
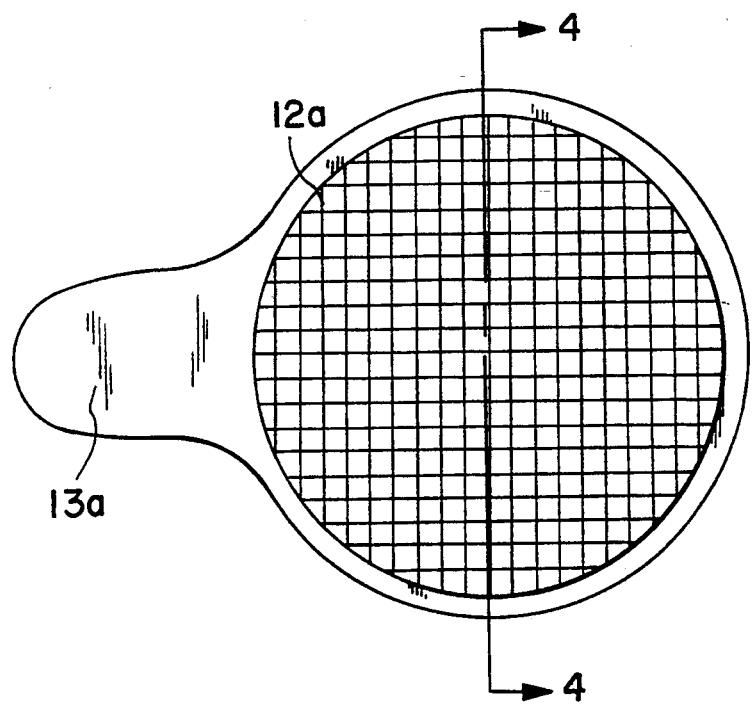
FIG. 3 is a top view of the adsorber shown in FIG. 2.
Figure 4:
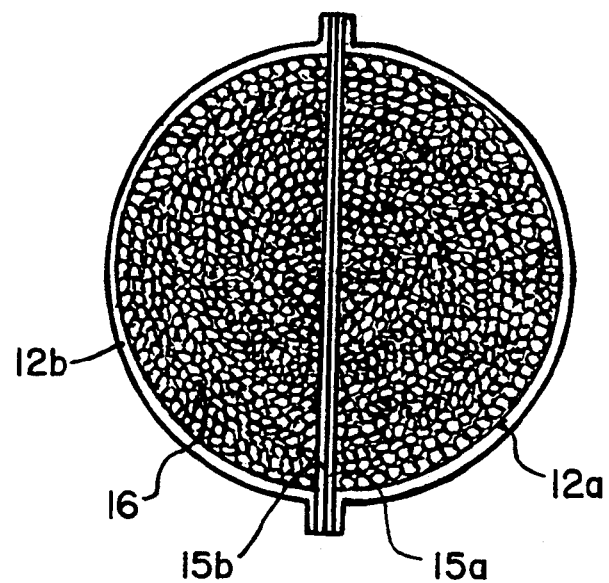
FIG. 4 is a cross sectional view along line 4—4 of the adsorber shown in FIG. 3.
Figure 5A:
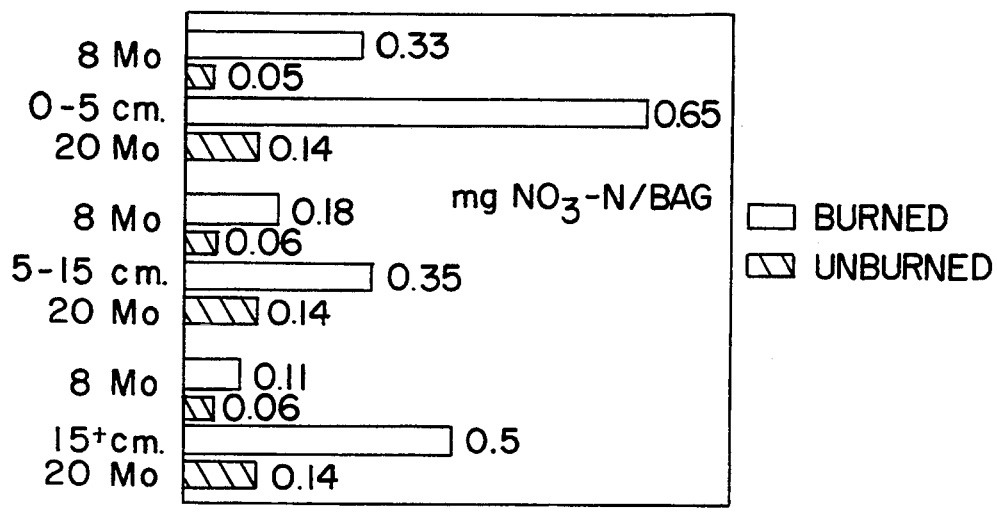
FIGS. 5A–5F are graphs showing the nutrients absorbed by the adsorber devices according to Example 3.
Figure 5B:
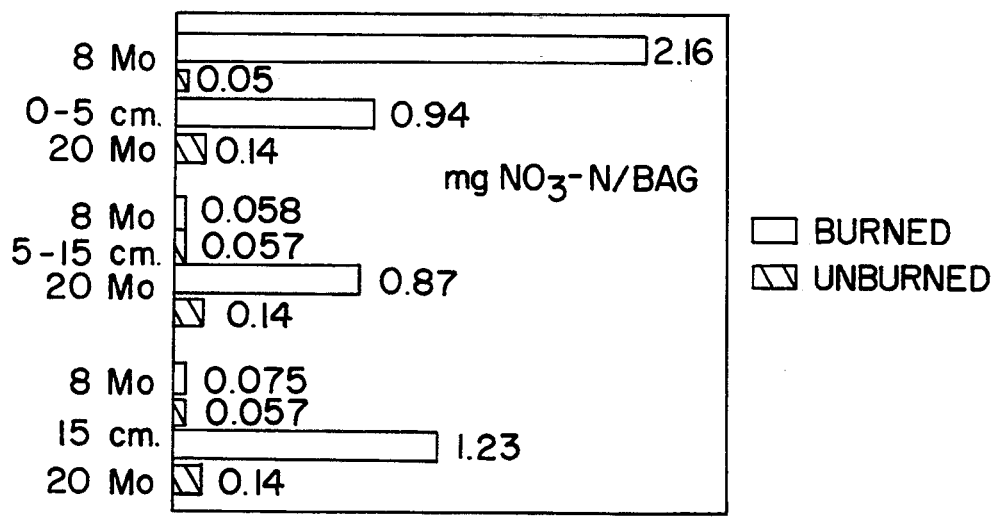
Figure 5C:
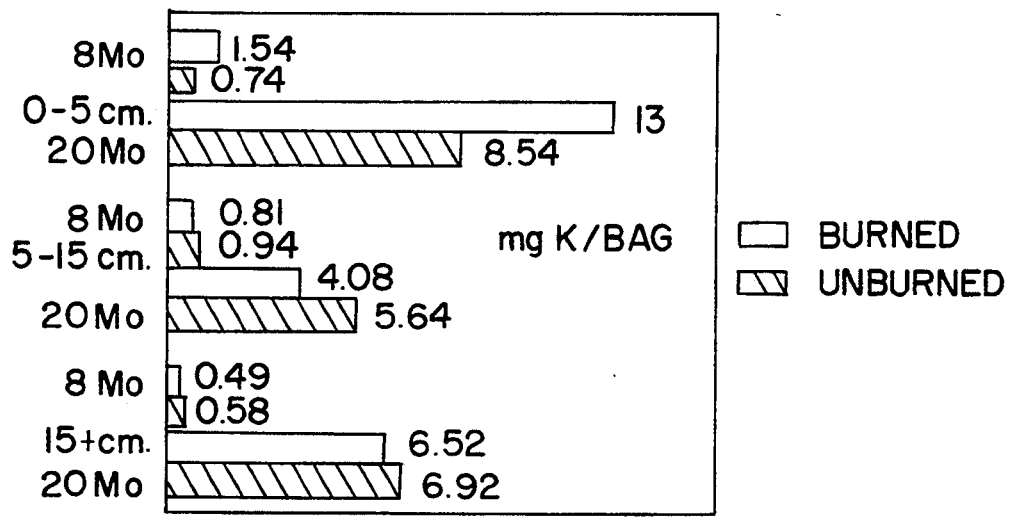
Figure 5D:
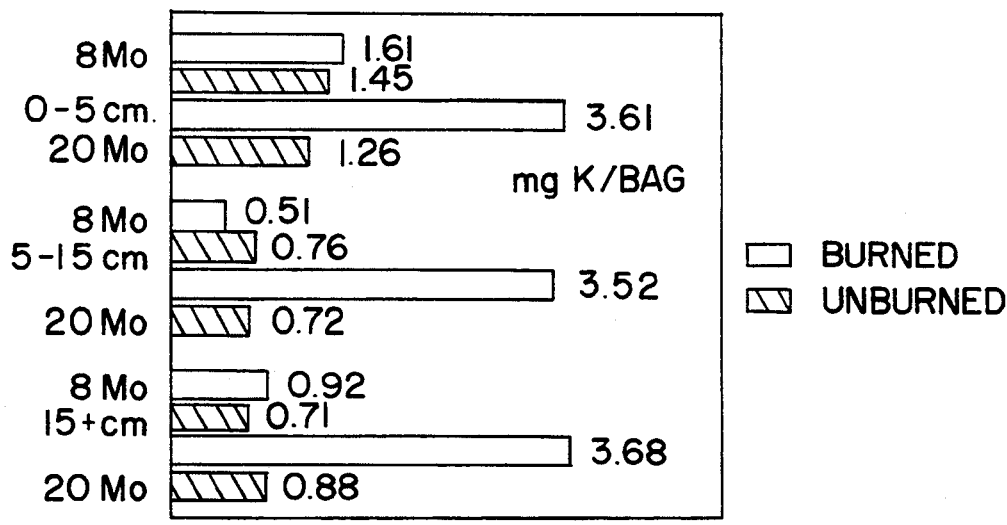
Figure 5E:
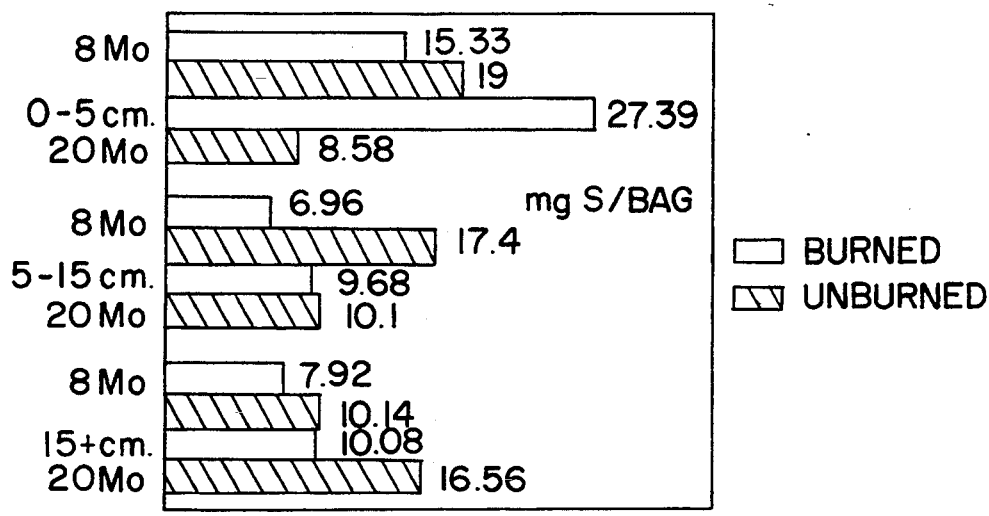
Figure 5F:
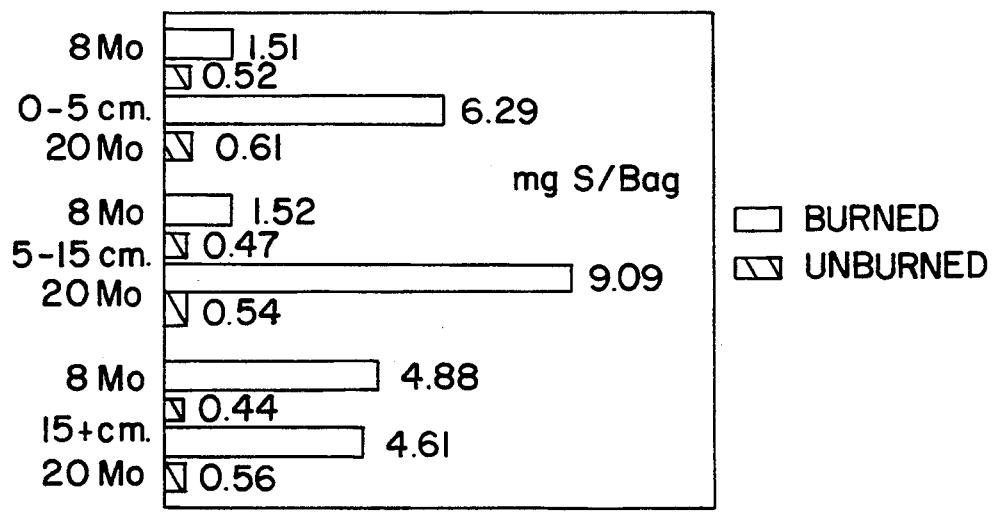
Figure 6A:
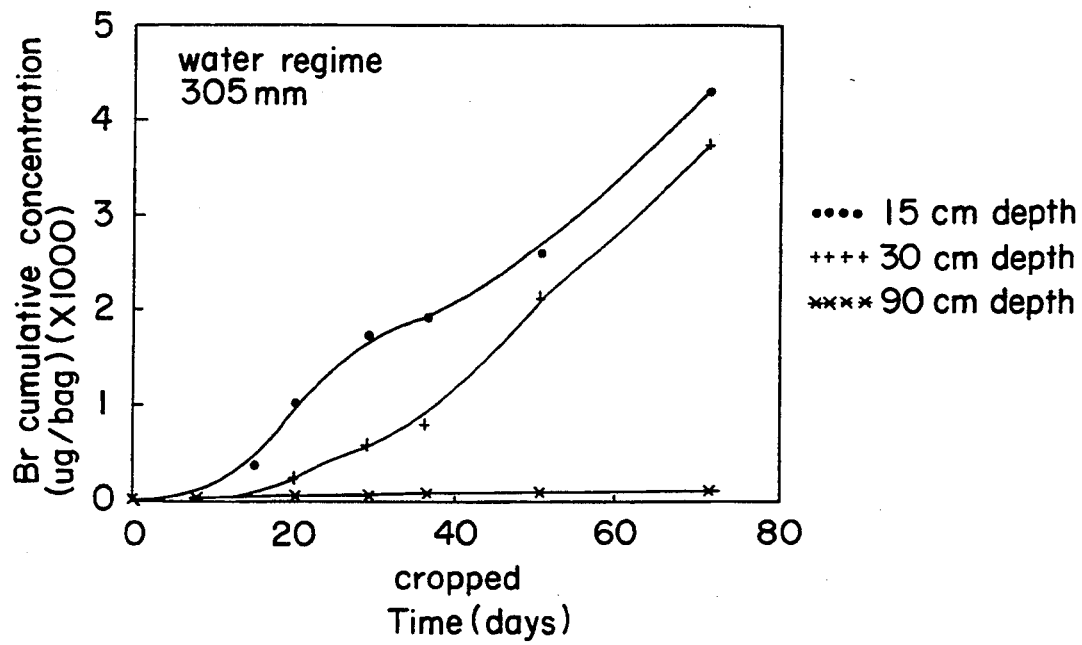
FIGS. 6A–6F are graphs of solute movement through soils as influenced by water movement according to Example 4.
Figure 6B:
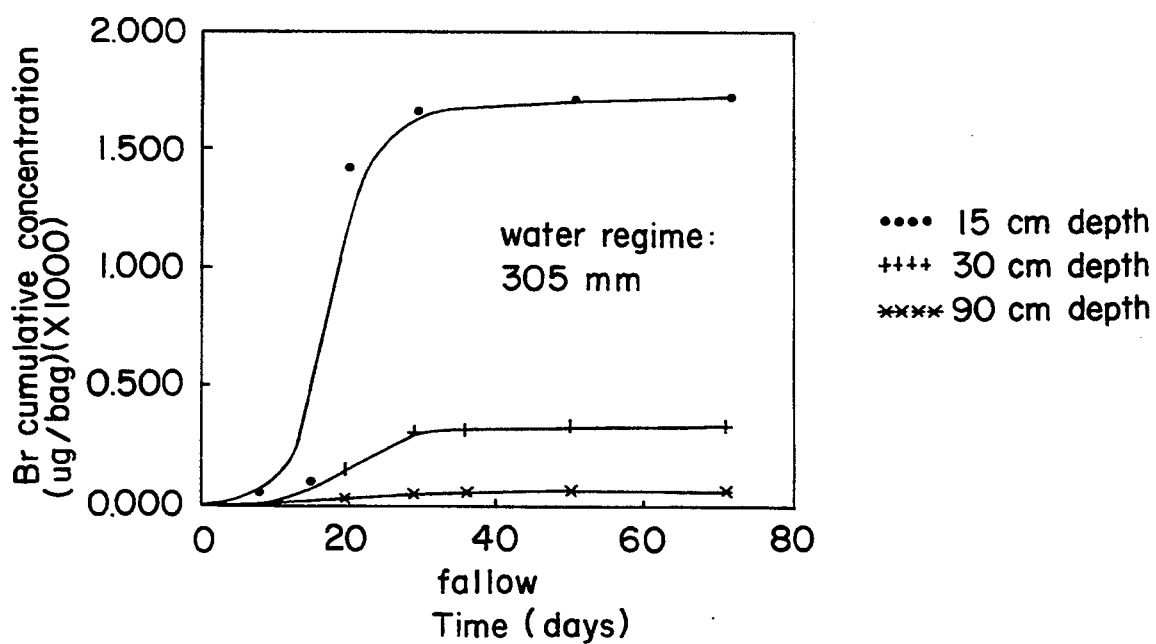
Figure 6C:
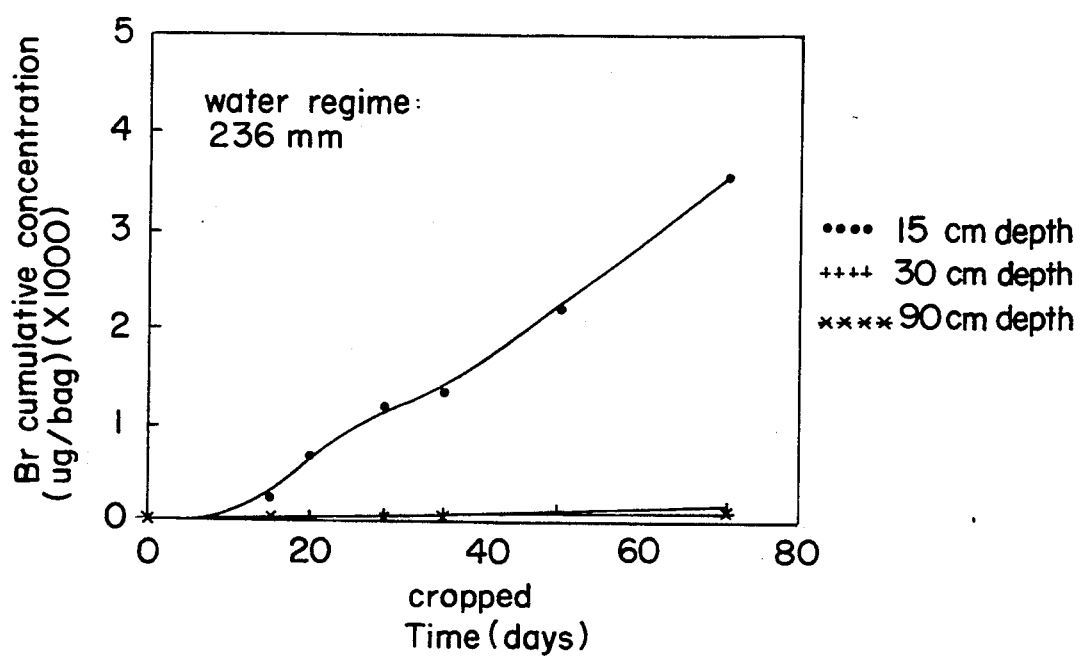
Figure 6D:
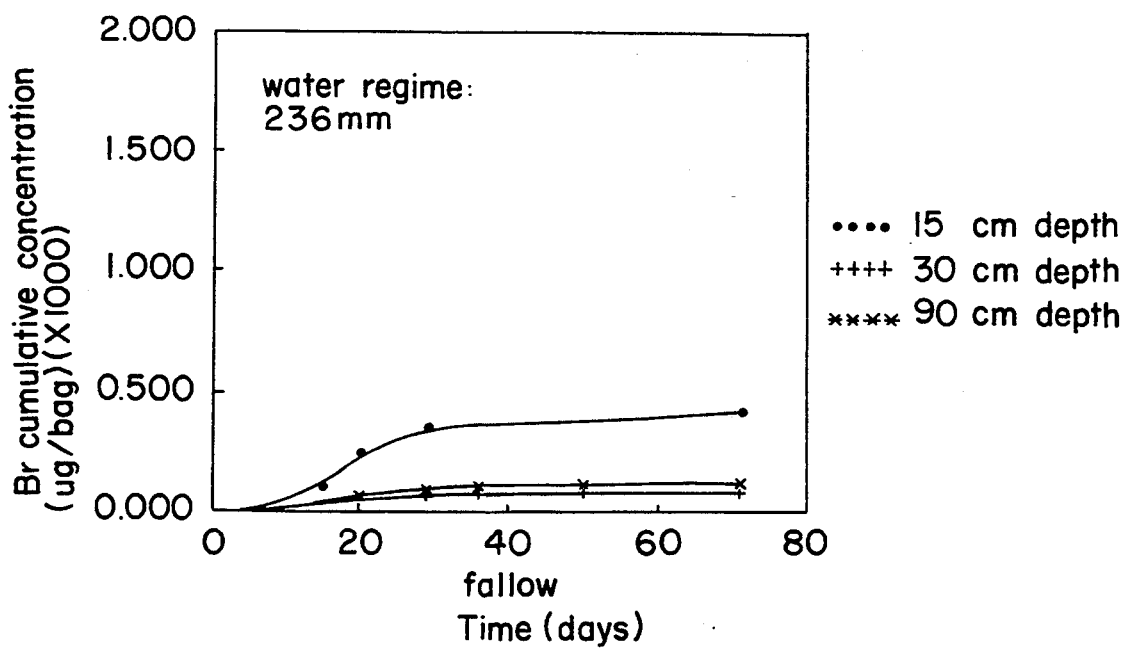
Figure 6E:
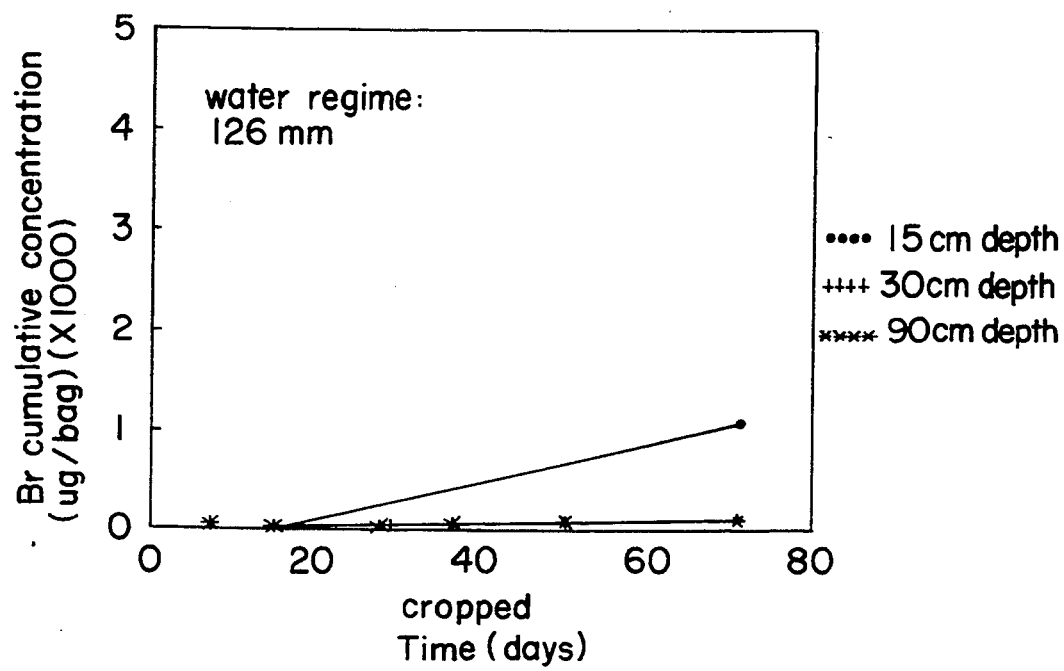
Figure 6F:
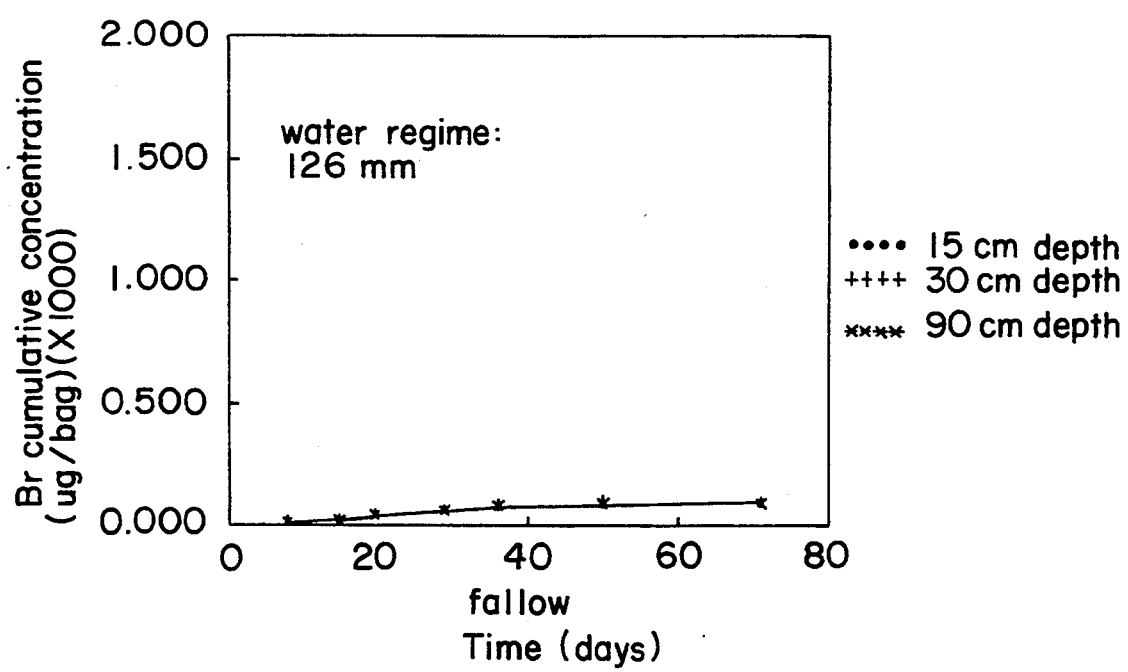
Figure 7A:
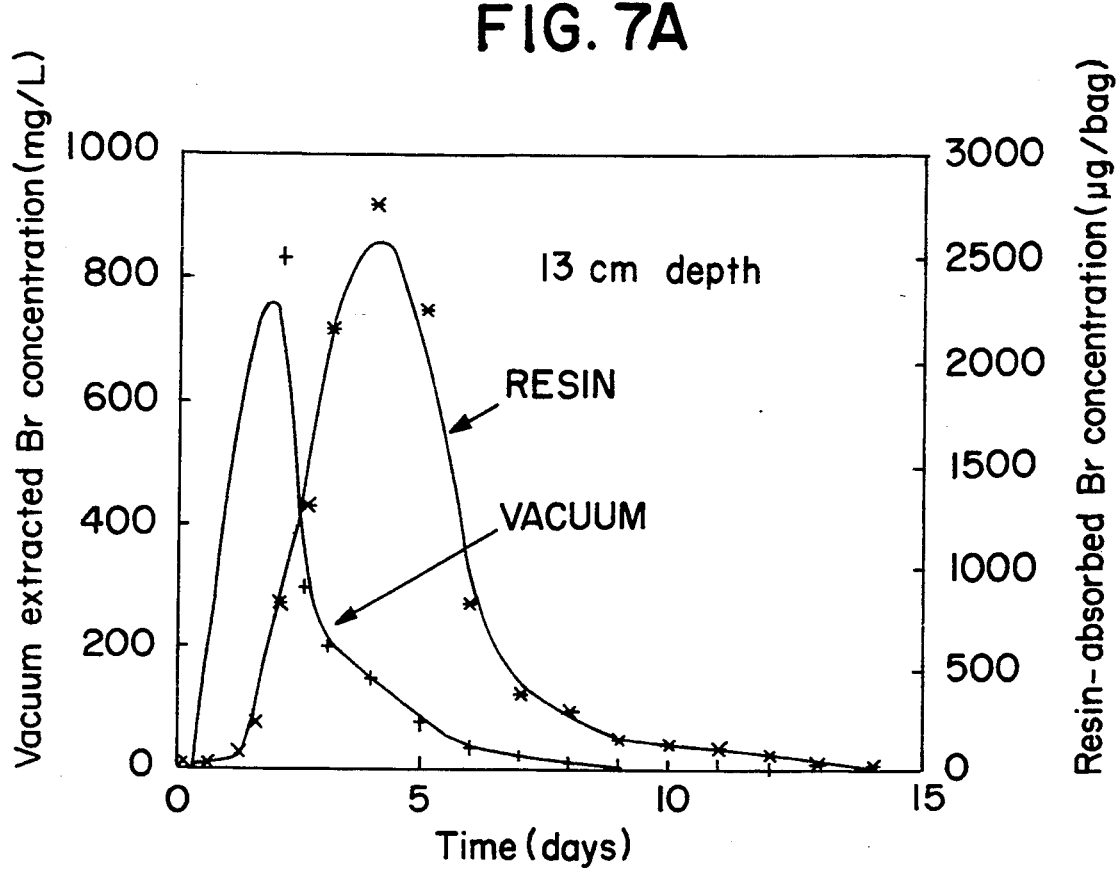
FIGS. 7A–7D are graphs of a comparison of the effectiveness of using adsorber devices as compared with vacuum extraction technology according to Example 5.
Figure 7B:
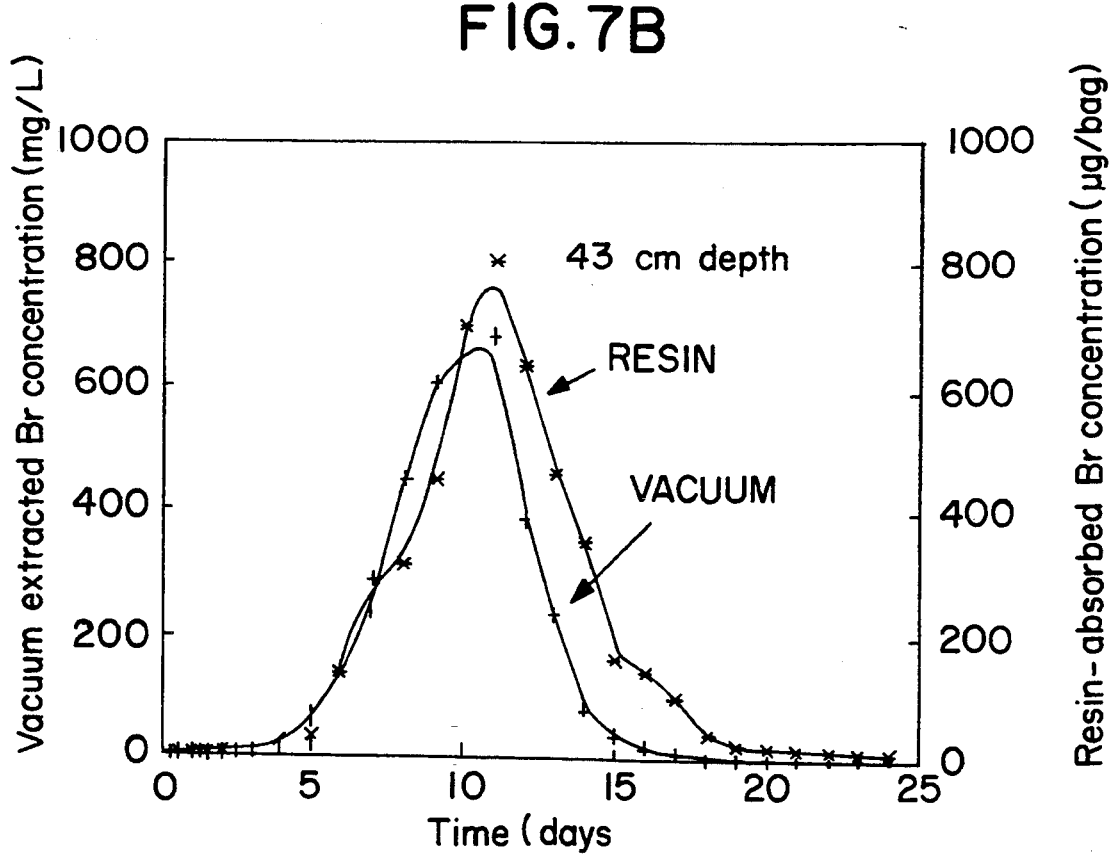
Figure 7C:
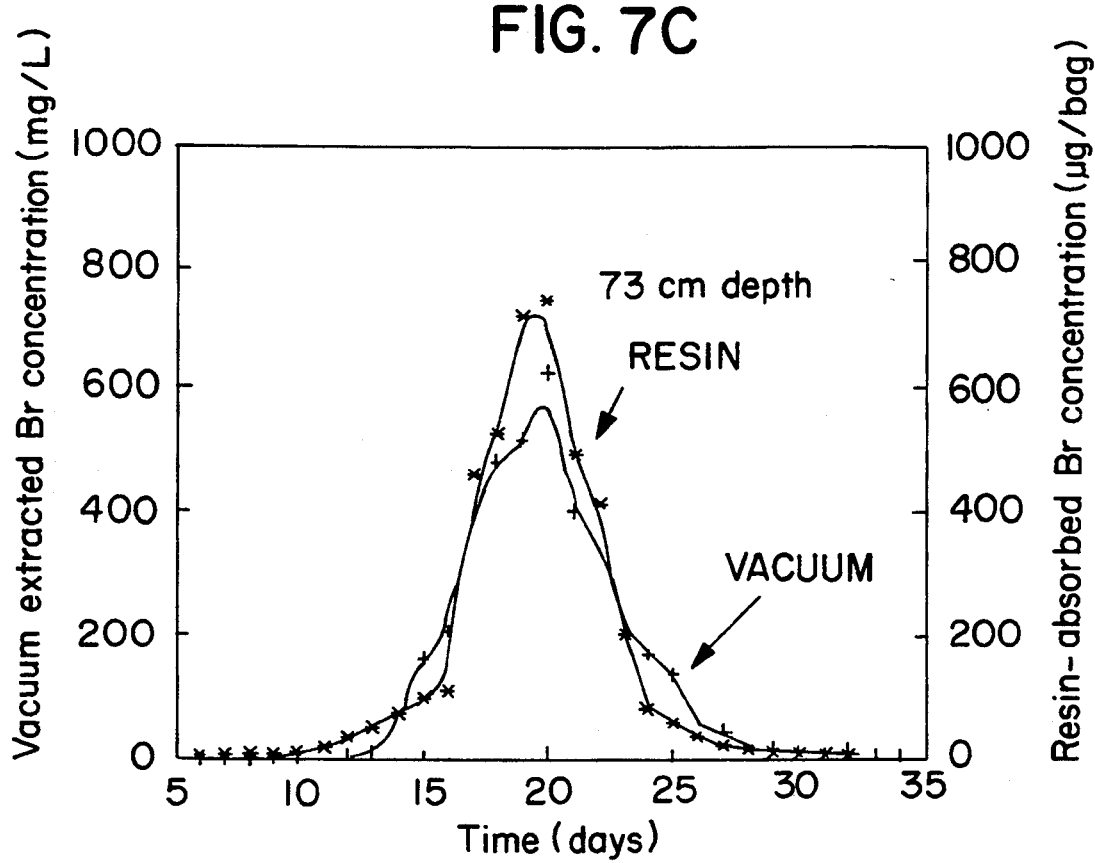
Figure 7D:
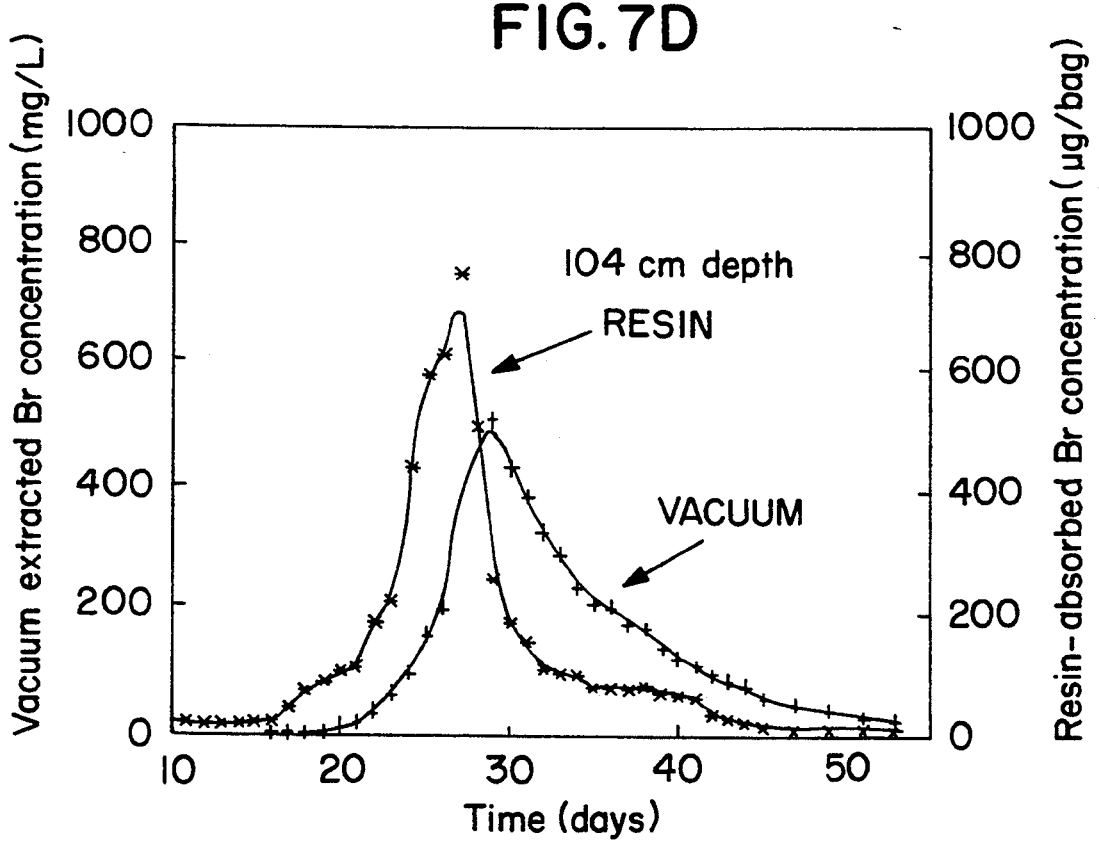

A preferred embodiment of adsorber device 10 is shown in FIG. 1. In a preferred embodiment the adsorber device 10 has a spherical shape, although other shaped devices may be made. In a preferred embodiment the adsorber device 10 is manufactured from two hollow semi-spherical shells 12a and 12b each having a handling tab 13a and 13b. The two shells 12a and 12b are joined together to form a spherical capsule with a handling tab. The shell material is made of a material such as woven mesh or fibrous polyester fabric which has the capacity to retain its formed shape. The capsule manufactured in this manner has pores 14 through the exterior and interior surfaces of the capsule. It is desired to maintain a uniform surface geometry of multiple adsorber devices 10 to improve the "reproducibility" of test results.

Each semi-spherical shell 12a and 12b is filled with an adsorber material 16 such as, but not limited to, a synthetic ion exchange resin (such as AMBERLITE IRN-150), carbonaceous resin (such as AMBERSORB), or natural adsorbers (such as zeolite or cellulose). Other adsorbers may also be selected for a specific test. Hundreds of different adsorber materials are commercially available. A layer of material 15a and 15b of the same type of material as the shell material is welded over the concave opening of each half-sphere to hold the adsorber in place. A complete sphere is fabricated by uniting the two half-spheres with their concave openings facing each other through ultrasonic or heat welding.

In use, multiple adsorber devices 10 of uniform size are placed in a test medium such as agricultural soil, contaminated soil, groundwater or standing water. Depending on the adsorber material 16 selected, the adsorber devices 10 may be used to accumulate diffusible solutes from the surrounding test medium, accumulate ions from free-water sources, accumulate non-ionized molecules from soils or other media through hydrophobic absorption or adsorb chemicals such as hydrocarbons.

After accumulating solutes (ions, chemicals, or organic molecules) for an elapsed test time, the adsorber devices 10 are recovered, and any attached surface material (such as loose soil) rinsed off with purified water. Then various alternative methods may be used to recover and quantitatively analyze the solutes accumulated by the adsorber device. For example, the adsorber material 16 containing the solutes may be leached with a strong acid (such as 2 molar hydrochloric acid) a base, or a salt solution to transfer all collected solutes from the adsorber material to an extract solution. For some tests, the adsorber with its accumulated solutes can be "ashed" at a high temperature and the resulting ash taken up in acid or other solution for analysis.

The extract solution may then be subjected to any of a wide variety of methods to determine the concentration of elements of interest. The results of this analysis may then be used as data in a computer program or otherwise evaluated to determine the underlying characteristics of the medium within which the free-standing adsorbers were placed. Since the shells 12 are of uniform shape and size, test results are reproducible and can be quantitatively calibrated.

To further demonstrate the manufacture of the improved adsorber and its use in operation, the following specific examples are included:

EXAMPLE 1

Method of Manufacturing the Adsorber

The adsorber device is manufactured through the use of a heated male-female, half-sphere die set with pin guides. By using the half-sphere dies, shell material is pressed into half-sphere shapes. Each half-sphere is filled with a desired adsorber. A layer of material of the same type as the shell material is welded over the half-sphere to hold the adsorber in place. A complete sphere is fabricated by uniting the two half-spheres through ultrasonic, or heat welding. Excess fabric is trimmed resulting in a uniform, spherical device filled with adsorber. Shell materials which have been used for the half-spheres include semi-rigid materials such as polyester, polypropylene, Teflon or Nylon. Either woven mesh or fibrous material may be used, as long it provides for free flow of liquids across it and allows the diffusion of solutes to freely occur. The standard size of the adsorber device is approximately 1.9 centimeter diameter providing for a volume of about 3.6 cubic centimeters of adsorber. The primary material used as the adsorber is a synthetic ion exchange resin such as AMBERLITE IRN-150.

EXAMPLE 2

Alternate Method of Construction

An alternate method of construction of the adsorber is to construct a hollow spherical capsule of shell material and then fill the capsule with adsorber material by injecting the adsorber material into the capsule through an access port. The access port would then be sealed to prevent adsorber leakage from the filled adsorber.

EXAMPLE 3

Further Examples of Actual Tests Using Adsorbers

Two sites on two different soil parent materials were selected in Yellowstone National Park immediately following the extensive 1988 forest fires. Paired locations at each site were chosen for comparison of nutrient dynamics, as measured by adsorber devices, on burned vs unburned soils. Small trenches were opened at each site to the depth of the soil (46 cm at one site and 60 cm at the other). Adsorber devices (each containing about 15 cc of AMBERLITE IRN-150 ion exchange resin, Rohm and Haas Co., Philadelphia, Pa.) were embedded about 5 cm into the face of each of three replicated pits at each of three depths. The adsorbers were in the upslope position so that they would intercept solutes moving through undisturbed soil. Cords attached to each capsule were strung to the soil surface to facilitate relocating them. Each trench was then closed in a manner to closely represent its initial condition. One set of adsorber devices was retrieved, by re-opening the trenches, at 8 months, 20 months, 24 months, and 32 months. The accumulated nutrients were desorbed from the adsorber devices and analyzed to determine differences in nutrient cycling as influenced by the forest burn on the two soils with different parent materials. A sample of results from this study are presented in FIGS. 5A–5F. These results indicate that the adsorber devices are sensitive to nutrient dynamics in different soils as influenced by intense forest burns.

EXAMPLE 4

Further Examples of Actual Tests Using Adsorbers

Another test of the adsorber devices was established on an agricultural field equipped with a "line-source" irrigation system to provide differential water application regimes. Access tubes made of PVC tubing were installed at approximately 60 degrees from the horizontal to selected depths in the soil. A cavity was made into the soil extending several cm beyond the end of the access tube. Into this access tube, a smaller PVC tube with an adsorber device (each containing about 5 cc of AMBERLITE IRN-150 ion exchange resin) attached to the end, was inserted and the adsorber pushed tightly into the soil cavity. Exactly one-half of the adsorber device was in contact with the soil so that a constant, known surface of contact was maintained. A solution of KBr was applied to the soil surface to provide a known amount of Br to act as a "tracer" which moves through the soil with water. This system was installed at five water regimes, ranging from excess irrigation to dryland. Adsorber devices were removed at approximately 2-week intervals, with new ones replacing the used ones. Accumulated Br was desorbed and analyzed to determine the sensitivity of this system for measuring solute movement through soils as influenced by water movement. Sample results are shown in FIGS. 6A–6F. These results illustrate that the adsorber devices provide data to measure solute transfer dynamics as influenced by different rates of water movement through the soil.

EXAMPLE 5

Further Examples of Actual Tests Using Adsorbers

A laboratory study was conducted to compare the adsorber device with a standard method of measuring solute dynamics in soils. A column 20 cm in diameter and 150 cm depth was packed with Brocko silt loam soil. The column was fitted with porous ceramic cups on one side to allow vacuum extraction of soil solutions at selected depths. At the same depths on the opposite side of the column, ports were installed to allow placement and retrieval of adsorber devices. Water was applied at a tension of $-17$ mbar. Once the water front reached the bottom of the column, a constant vacuum of $-400$ mbar was maintained at the bottom, providing a system for unsaturated water flow at a rate of 1.4 cm/day. A solution of KBr was sprayed on the surface to provide a known amount of Br to act as a tracer. Soil solutions were extracted from four column depths at selected times and analyzed for Br (this is a standard method for studying solute movement in porous media). At the same time, adsorber devices (each containing about 5 cc of AMBERLITE IRN-150) were removed and a new one inserted. Quantities of Br accumulated by the adsorber were determined and compared with those measured by vacuum extraction. Samples results are shown in FIGS. 7A–7D. These results indicate that the adsorber devices provide a method of studying solute transfer through porous media, with equal or better sensitivity than the commonly used vacuum extraction methodology.

EXAMPLE 6

Further Examples of Actual Tests Using Adsorbers

A second laboratory column experiment was conducted to determine the utility of the adsorber devices for monitoring herbicide movement in porous media. A soil column was prepared by packing 710 g of moist Amsterdam silt loam soil into a plexiglas column 5 cm in diameter and 30 cm long. The column system was manipulated in a manner similar to that described above to provide unsaturated water flow. The column has two ports, one at 3 cm from the surface and the other at 23 cm, through which small adsorber devices (about 1.25 cm in diameter and containing about 1.7 cc of AMBERLITE IRN-150 ion exchange resin) could be inserted and retrieved. A solution containing radioactively tagged picloram (Tordon) was applied to the surface. Water was surface applied and moved through the column under unsaturated conditions. At hourly intervals, the adsorber device was removed and a new one inserted at each of the two column ports. Amounts of Tordon adsorbed were determined by detection of the radioactivity of each adsorber after one hour of contact with the soil column over a 14 hour period. Results are presented in FIG. 8. The breakthrough curve for Tordon at the two column depths was characteristic of curves determined by vacuum extraction methodologies.

These sample experiments and results provide an indication of the broad range of problems to which the adsorber device methodology can be applied.

While the fundamental novel features of the invention have been shown and described, it should be understood that various substitutions, modifications and variations may be made by those skilled in the art without departing from the spirit or scope of the invention.

Accordingly, all such modifications or variations are included in the scope of the invention as defined by the following claims.

I claim:

1. A free standing, self contained solute adsorber device comprising:
    a pair of hollow, semi-spherical shells being joined together to form a hollow, spherical capsule;
    the semi-spherical shells being formed of a porous, shape retaining material;
    the adsorber device having an adsorber material held within the capsule.

2. An adsorber device according to claim 1 wherein the shells are constructed with a woven mesh fabric.

3. An adsorber device according to claim 1 wherein the adsorber material comprises a synthetic ion exchange resin.

4. An adsorber device according to claim 1 wherein the shells are constructed of a fibrous polyester fabric.

5. An adsorber device according to claim 1 wherein the adsorber material comprises a carbonaceous resin.

6. An adsorber device according to claim 1 wherein the adsorber material comprises a naturally occurring adsorber.

7. A process for recovering solutes from a medium comprising:
    the scattering of multiple adsorber devices throughout the medium from which solutes are to be recovered, each adsorber device having a hollow spherical semi-rigid capsule made of porous material and having an interior and exterior surface with pores extending between the interior surface and the exterior surface and the capsule being filled with an adsorber material; and
    recovering the adsorber devices.

8. A process for analyzing the quantity of solutes in a medium comprising:
    the scattering of multiple adsorber devices throughout the medium from which solutes are to be recovered, each adsorber device having a hollow spherical semi-rigid capsule made of porous material and having an interior and exterior surface with pores extending between the interior surface and the exterior surface and the capsule being filled with an adsorber material;
    recovering the adsorber devices; and
    recovering the solutes from the adsorber material into an extract solution; and
    performing an analysis of the solutes in the extract solution.

9. A process for analyzing the diffusion rate of solutes in a medium comprising:
    the scattering of multiple adsorber devices throughout the medium from which solutes are to be recovered, each adsorber device having a hollow spherical semi-rigid capsule made of porous material and having an interior and exterior surface with pores extending between the interior surface and the exterior surface and the capsule being filled with an adsorber material;
    recovering the adsorber devices after a predetermined period of time; and
    recovering the solutes from the adsorber material into an extract solution; and
    performing an analysis of the solutes in the extract solution.

* * * * *

UNITED STATES PATENT AND TRADEMARK OFFICE
CERTIFICATE OF CORRECTION

PATENT NO. : 5,355,736

DATED : October 18, 1994

INVENTOR(S) : Earl O. Skogley

It is certified that error appears in the above—identified patent and that said Letters Patent is hereby corrected as shown below:

Title Page & Column 1, line 1
Title of Invention: Change "Absorber" to --Adsorber--.

Signed and Sealed this

Seventh Day of February, 1995

Attest:

BRUCE LEHMAN

Attesting Officer

Commissioner of Patents and Trademarks